US00PP09251P

United States Patent [19]

Meilland

[11] Patent Number: Plant 9,251

[45] Date of Patent: Aug. 22, 1995

[54] SHRUB ROSE PLANT NAMED 'MEIRUMOUR'

[75] Inventor: Alain A. Meilland, Antibes, France

[73] Assignee: The Conard-Pyle Company, West Grove, Pa.

[21] Appl. No.: 314,390

[22] Filed: Sep. 28, 1994

[51] Int. Cl.[6] ..... H01H 5/00

[52] U.S. Cl. ..... Plt./1

[58] Field of Search ..... Plt. 1, 22

[56] References Cited

U.S. PATENT DOCUMENTS

P.P. 3,985 11/1976 McGredy ..... Plt./1
P.P. 5,956 4/1987 Meilland ..... Plt./1
P.P. 6,577 1/1989 Warriner ..... Plt./1
P.P. 7,116 1/1990 Meilland ..... Plt./1

*Primary Examiner*—Howard J. Locker
*Attorney, Agent, or Firm*—Burns, Doane, Swecker & Mathis

[57] ABSTRACT

A new and distinct variety of shrub rose plant is provided which forms continuously throughout the season attractive simple long-lasting blossoms that are Guardsman Red with a white eye on the upper surface. The blossom petals are white suffused and edged with Carmine Red on the under surface and detach cleanly. The plant possesses a bushy growth habit. The new variety exhibits excellent resistance to Marssonina disease, and is well suited for use as attractive ornamentation in the landscape.

1 Drawing Sheet

SUMMARY OF THE INVENTION

The new variety of shrub rose plant of the present invention was created by artificial pollination wherein two parents were crossed which previously had been studied in the hope that they would contribute the desired characteristics. The female parent (i.e., the seed parent) was the Meipoque variety (U.S. Plant Pat. No. 5,956). The male parent (i.e., the pollen parent) of the new variety was the product of the pollination of the Regensberg variety (non-patented in the United States) and the Fair Play variety (non-patented in the United States). The Regensberg variety sometimes is known as the MACyoumis variety. The parentage of the new variety can be summarized as follows:

Meipoque × (Regensberg × Fair Play).

The seeds resulting from the above pollination were sown and 45 small plants were obtained which were physically and biologically different from each other. Selective study resulted in the identification of a single plant of the new variety.

It is found that the new variety of shrub rose plant possesses the following combination of characteristics:

(a) forms continuously throughout the season attractive simple blossoms which are Guardsman Red with a white eye on the upper surface and are white suffused and edged with Carmine Red on the under surface,
(b) exhibits a bushy growth habit, and
(c) exhibits excellent resistance to Marssonia disease.

The new variety meets the needs of the horticultural industry and can be grown to particular advantage as attractive ornamentation in parks, gardens, public areas, and residential landscapes.

The new variety of the present invention has been found to undergo asexual propagation by a number of routes in France including budding, grafing and cuttings. Axexual propagation by the above-mentioned routes as performed in France has shown that the characteristics of the new variety are homogeneous and stable and are strictly transmissible from one generation to another.

The new variety has been named the Meirumour variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were four years of age and were observed during June while growing on their own roots outdoors at Le Cannet des Maures, Var, France.

DETAILED DESCRIPTION

Figures 1, 2, 3, 4, 5, 6, 7, 8, 9, 10, 11, 12, 13, 14, 15, 16, 17:
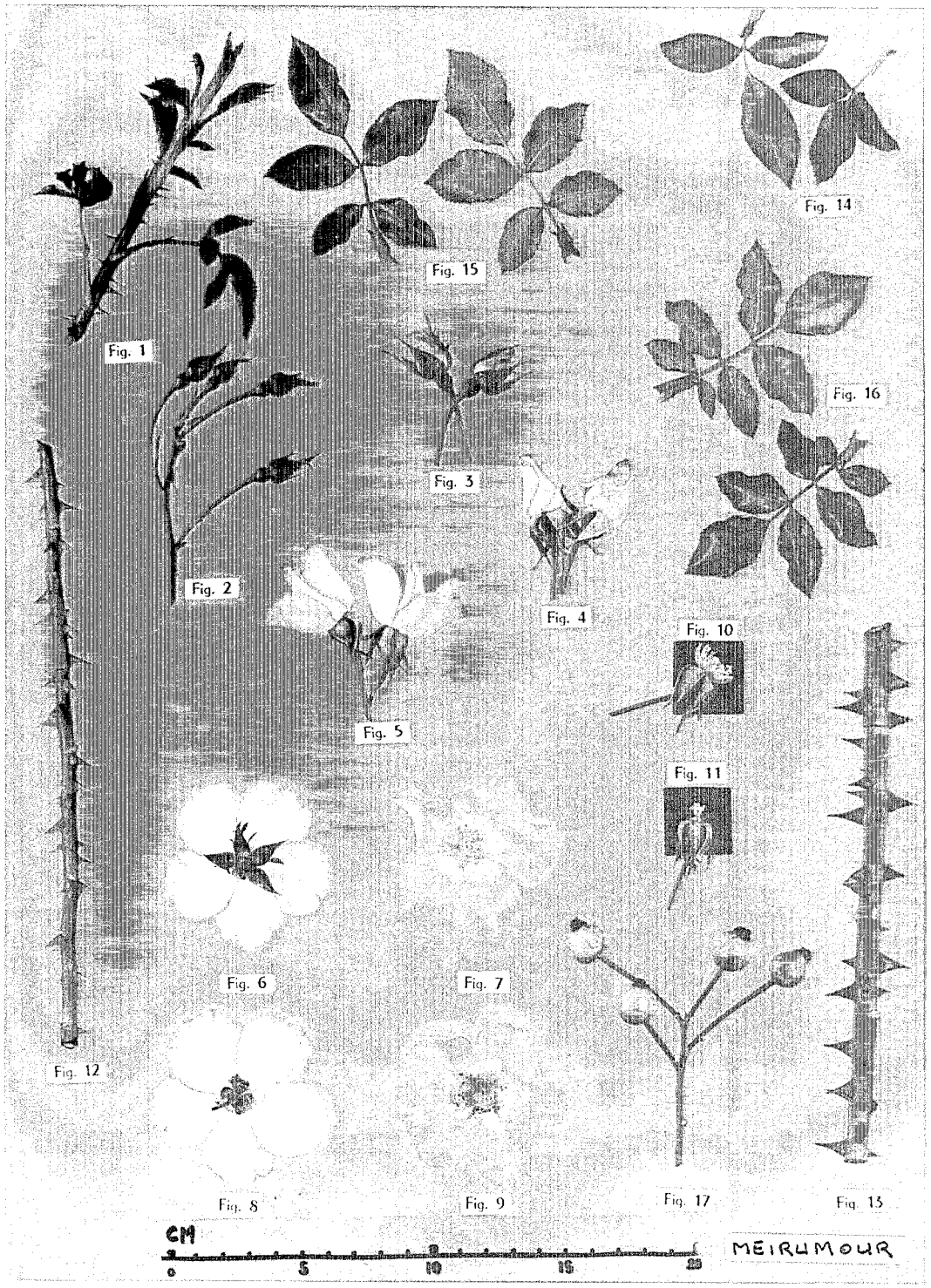
FIG. 1 illustrates a specimen of a young shoot.
FIG. 2 illustrates a specimen of four floral buds before the opening of the sepals.
FIG. 3 illustrates specimens of two floral buds as the sepals open.
FIG. 4 illustrates specimens of two floral buds as the petals open.
FIG. 5 illustrates specimens of two flowers in the course of blooming.
FIG. 6 illustrates a specimen of a open flower—plan view—reverse.
FIG. 7 illustrates a specimen of a open flower—plan view—obverse.
FIG. 8 illustrates a specimen of a fully open flower—plan view—reverse.
FIG. 9 illustrates a specimen of a fully open flower—plan view—obverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets—upper (right) and under (left) surfaces.
FIG. 15 illustrates specimens of leaves with five leaflets—upper (left) and under (right) surfaces.
FIG. 16 illustrates specimens of leaves with seven leaflets—plan view—upper (at bottom) and under (at top) surfaces.
FIG. 17 illustrates a specimen of four fruits.

The chart used in the identification of the colors is that of the Royal Horticultural Society (R.H.S. Colour Chart). The terminology preceding the numbered reference to the chart has been added to indicate in more common terms the corresponding color. The description is based on the observation of four year-old specimens of the new variety while grown outdoors on their own roots during October at Le Cannet des Maures, Var, France.

Class: Shrub.

Plant:

*Height.*—Approximately 80 cm. on average at the end of the growing season.

*Habit.*—Bushy.

Branches:

*Color.*—Young stems: medium green, Green Group 143B and widely suffused with reddish coloration. Adult wood: light green, Green Group 146C.

*Thorns.*—Size: medium. Quantity: moderately numerous. Color: on young stems reddish with some green coloration on the top, and pinkish/-greenish on adult wood.

Leaves:

*Stipules.*—Adnate, pectinate, and moderately wide linear.

*Petioles.*—Upper surface: striped reddish brown on young foliage and medium green on adult foliage with more or less glandular edges. Under surface: light green with some prickles.

*Leaflets.*—Number: 3, 5 (most often), and 7. Shape: oval. Serration: as illustrated. Texture: rather consistent. General appearance: dense and semi-dull foliage. Color (young foliage): Upper surface: bronze green, Yellow-Green Group 146A and more or less suffused with reddish brown. Under surface: medium green, Yellow-Green Group 147B and more or less suffused with reddish brown. Color (adult foliage): Upper surface: dark green, Yellow-Green Group 147A. Under surface: medium green, Yellow-Green Group 147B.

Inflorescence:

*Number of flowers.*—Approximately 1 to 12 flowers per stem.

*Peduncle.*—Medium green, more or less tinted with reddish coloration and bears numerous pediculate glands, approximately 1.5 cm. in length on average.

*Sepals.*—Upper surface: tomentose, and greenish in coloration. Under surface: medium green with a more or less reddish tint and the edges are more or less appendiculated.

*Buds.*—Shape: oval. Length: approximately 1.5 cm. on average. Size: medium for this rose class. Color when opening: Upper surface: Guardsman Red, Red Group 45A, with white eye. Under surface: Guardsman Red, Red Group 45A, with white eye.

*Flower.*—Form: opens as a flat cup. Diameter: approximately 5 cm. on average. Color (when opening begins): Upper surface: Guardsman Red, Reg Group 45A, with white eye. Under surface: whitish and more or less suffused and edged with Carmine Red, Red Group 52B. Color (when blooming): Upper surface: Guardsman Red, Red Group 45A, with white eye as illustrated. Under surface: whitish and more or less suffused and edged with Carmine Red, Red Group 52 B. Color (at end of opening): Upper surface: Guardsman Red, Red Group 45A, with white eye as illustrated. Under surface: whitish and more or less suffused and edged with Carmine Red, Red Group 52B. Fragrance: none. Lasting quality: very long. Petal form: rounded and sometimes indented at tip. Texture: firm. Petal number: commonly 5. Petal drop: good. Stamen number: approximately 121 on average. Anthers: light ochre and edged with fuchsine coloration. Filaments: fuchsine coloration and well arranged around the receptacle. Pistils: approximately 26 to 28 on average. Stigmas: normal and yellowish in coloration. Styles: light fuchsine in coloration and very short. Receptacle: medium green and smooth and in longitudinal section it is in the shape of a thin pear.

Development:

*Vegetation.*—Strong.

*Blooming.*—Very abundant and continuous.

*Aptitude-to bear fruits.*—Good.

*Resistance to diseases.13* Very good with excellent resistance to Marssonina disease.

I claim:

1. A new and distinct variety of shrub rose plant characterized by the following combination of characteristics:

(a) forms continuously throughout the season attractive simple blossoms which are Guardsman Red with a white eye on the upper surface and are white suffused and edged with Carmine Red on the under surface, (b) exhibits a bushy growth habit, and (c) exhibits excellent resistance to Marssonina disease;

substantially as herein shown and described.

* * * * *

CM
0
5
10
15
20
MEIRUMOUR